US011704800B2

United States Patent
Murray et al.

(10) Patent No.: US 11,704,800 B2
(45) Date of Patent: *Jul. 18, 2023

(54) METHODS AND APPARATUS FOR DETECTING INJURY USING MULTIPLE TYPES OF MAGNETIC RESONANCE IMAGING DATA

(71) Applicant: Voxel AI, Inc., Toronto (CA)

(72) Inventors: Christopher I. Murray, Kingston (CA); Andrew N. Ross, Toronto (CA); Douglas J. Cook, Toronto (CA)

(73) Assignee: Voxel AI, Inc., Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/870,446

(22) Filed: Jul. 21, 2022

(65) Prior Publication Data

US 2022/0358657 A1 Nov. 10, 2022

Related U.S. Application Data

(63) Continuation of application No. 17/604,151, filed as application No. PCT/IB2020/000276 on Apr. 16, 2020, now Pat. No. 11,423,543.

(Continued)

(51) Int. Cl.
*G06T 7/00* (2017.01)
*G06T 7/11* (2017.01)
(Continued)

(52) U.S. Cl.
CPC .......... *G06T 7/0014* (2013.01); *A61B 5/0042* (2013.01); *A61B 5/055* (2013.01);
(Continued)

(58) Field of Classification Search
CPC .......... G06T 5/50; G06T 7/0014; G06T 7/11; G06T 2207/10088; G06T 2207/20212;
(Continued)

(56) References Cited

U.S. PATENT DOCUMENTS

| 10,357,217 B2 * | 7/2019 | Huang | A61B 5/4088 |
| 11,324,413 B1 * | 5/2022 | Benson | G01R 33/5602 |

(Continued)

FOREIGN PATENT DOCUMENTS

| WO | 2016086289 A1 | 6/2016 | |
| WO | 2019172968 A1 | 9/2019 | |
| WO | WO-2019172968 A1 * | 9/2019 | ............. A61B 5/055 |

OTHER PUBLICATIONS

Extended European Search Report of the European Patent Office for Application No. 20791888.9-1113 dated Nov. 30, 2022.
(Continued)

*Primary Examiner* — Nay A Maung
*Assistant Examiner* — Jose M Torres
(74) *Attorney, Agent, or Firm* — Pierce Atwood LLP

(57) ABSTRACT

Methods and apparatus for evaluating an impact of injury to brain networks or regions are provided. The method comprises receiving MRI data of a brain of an individual, including a first volumetric dataset recorded using first imaging parameters and a second volumetric dataset recorded using second imaging parameters, combining, on a voxel-by-voxel basis, first MRI data based on the first volumetric dataset and second MRI data based on the second volumetric dataset to produce a volumetric injury map, performing a structural-functional analysis of one or more brain networks or regions by refining the volumetric injury map using a volumetric eloquence map that specifies eloquent brain tissue within the one or more brain networks or regions to determine an impact of injury within the one or more brain networks or regions, and displaying a visualization of the determined impact of injury within the one or more brain networks or regions.

28 Claims, 10 Drawing Sheets

Related U.S. Application Data

(60) Provisional application No. 62/835,223, filed on Apr. 17, 2019.

(51) Int. Cl.

| | | |
|---|---|---|
| *G16H 50/20* | (2018.01) | |
| *G16H 30/40* | (2018.01) | |
| *A61B 5/00* | (2006.01) | |
| *A61B 5/055* | (2006.01) | |
| *G01R 33/48* | (2006.01) | |
| *G01R 33/56* | (2006.01) | |
| *G06T 5/50* | (2006.01) | |

(52) U.S. Cl.
CPC ..... *G01R 33/4806* (2013.01); *G01R 33/5608* (2013.01); *G06T 5/50* (2013.01); *G06T 7/11* (2017.01); *G16H 30/40* (2018.01); *G16H 50/20* (2018.01); *G06T 2207/10088* (2013.01); *G06T 2207/20212* (2013.01); *G06T 2207/30016* (2013.01)

(58) Field of Classification Search
CPC ........ G06T 2207/30016; A61B 5/0042; A61B 5/055; G01R 33/4806; G01R 33/5608; G16H 30/40; G16H 50/20; G16H 50/50
See application file for complete search history.

(56) References Cited

U.S. PATENT DOCUMENTS

| | | |
|---|---|---|
| 2009/0030304 A1 | 1/2009 | Feiweier et al. |
| 2010/0080432 A1* | 4/2010 | Lilja ............... G06T 7/0012 382/131 |
| 2011/0160543 A1* | 6/2011 | Parsey ............... A61B 6/56 600/300 |
| 2013/0317341 A1 | 11/2013 | Spies |
| 2014/0219535 A1 | 8/2014 | Chen et al. |
| 2014/0270451 A1 | 9/2014 | Zach et al. |
| 2015/0110374 A1 | 4/2015 | Traughber et al. |
| 2015/0199121 A1 | 7/2015 | Gulaka et al. |
| 2015/0324994 A1* | 11/2015 | Tseng ............... G06T 7/0002 382/128 |
| 2018/0025489 A1 | 1/2018 | Tiwari et al. |
| 2019/0180878 A1* | 6/2019 | Fridriksson ......... G16H 50/70 |

OTHER PUBLICATIONS

Vergun, et al., "Predicting Primary Outcomes of Brain Tumor Patients With Advanced Neuroimaging MRI Measures", Interdisciplinary Neurosurgury, vol. 13, Sep. 1, 2018; pp. 109-118.

International Search Report and Written Opinion dated Sep. 2, 2020 in connection with International Application No. PCT/IB2020/000276.

Goh, et al., "Neuroinformatics challenges to the structural, connectomic, functional, and electrophysiological multimodal imaging of human traumatic brain injury", (Frontiers in Neuroinformatics), Feb. 26, 2014, vol. 8, Article 19, pp. 1-12.

* cited by examiner

FIG. 5A  Stroke Map — Blend of GMV, CBF and DTI data.

FIG. 5B  Eloquence map — Right executive control network

FIG. 5C  Stroke impact on network — 4.6% of network volume impacted by stroke lesion (Right Inferior Parietal, Supramarginal and Angular Gyri)

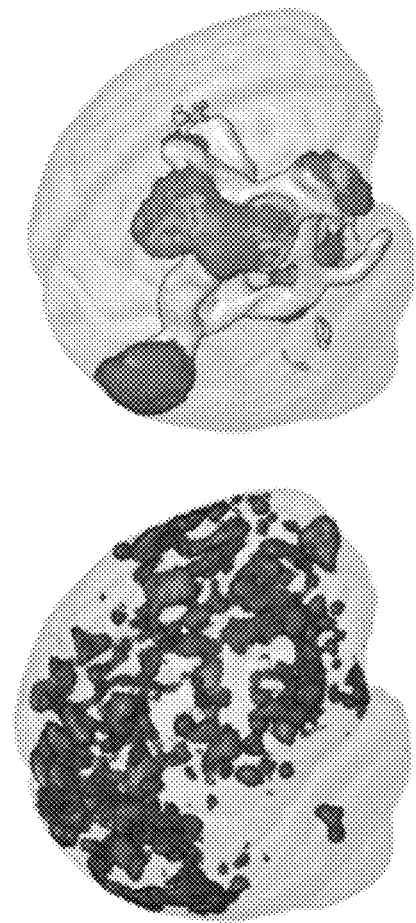
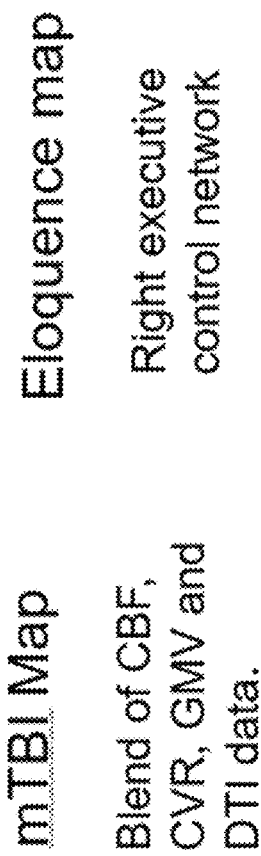
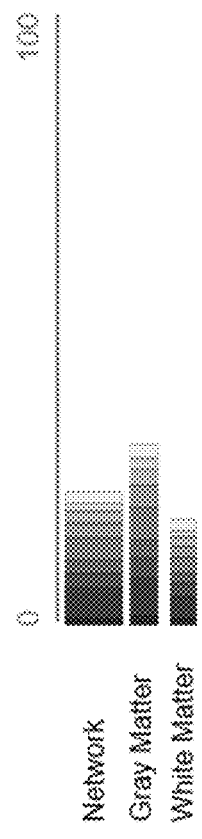
FIG. 7A — mTBI Map. Blend of CBF, CVR, GMV and DTI data.
FIG. 7B — Eloquence map. Right executive control network
FIG. 7C — mTBI impact on network

US 11,704,800 B2

METHODS AND APPARATUS FOR DETECTING INJURY USING MULTIPLE TYPES OF MAGNETIC RESONANCE IMAGING DATA

CROSS REFERENCE TO RELATED APPLICATIONS

This Application is a Continuation of U.S. application Ser. No. 17/604,151, filed Oct. 15, 2021, entitled, "METHODS AND APPARATUS FOR DETECTING INJURY USING MULTIPLE TYPES OF MAGNETIC RESONANCE IMAGING DATA," which is a national stage filing under 35 U.S.C. 371 of International Patent Application Serial No. PCT/M2020/000276, filed Apr. 16, 2020, entitled "METHODS AND APPARATUS FOR DETECTING INJURY USING MULTIPLE TYPES OF MAGNETIC RESONANCE IMAGING DATA," which claims the benefit under 35 U.S.C. § 119(e) of U.S. Provisional Patent Application Ser. No. 62/835,223, filed Apr. 17, 2019, entitled "METHODS AND APPARATUS FOR DETECTING INJURY USING MULTIPLE TYPES OF MAGNETIC RESONANCE IMAGING DATA," the entire contents of each of which is incorporated herein by reference in its entirety.

BACKGROUND

The brain is composed of grey and white matter. These tissue types are formed by the arrangement of approximately 100 billion highly organized, interconnected and communicating neurons. The neuron's cell bodies form the grey matter where signals are received and processed. Each cell body has a long axon that extends out and bundles with other axons to form the white matter tracts that transmit signals throughout the brain and out to the body. Analysis of the grey matter and/or white matter tracts may be used to evaluate the extent of brain injury caused, for example, by stroke, traumatic brain injury, or other neurological diseases.

SUMMARY

Some embodiments relate to a computerized system for evaluating an impact of injury to brain networks or regions. The system comprises at least one computer processor, and at least one computer-readable medium encoded with a plurality of instructions that, when executed by the at least one computer processor, perform a method of evaluating an impact of injury to one or more brain networks or regions. The method comprises receiving magnetic resonance imaging (MRI) data of a brain of an individual, wherein the MRI data includes a first volumetric dataset recorded using first imaging parameters and a second volumetric dataset recorded using second imaging parameters, combining, on a voxel-by-voxel basis, first MRI data based on the first volumetric dataset and second MRI data based on the second volumetric dataset to produce a volumetric injury map, performing a structural-functional analysis of one or more brain networks or regions by refining the volumetric injury map using a volumetric eloquence map that specifies eloquent brain tissue within the one or more brain networks or regions to determine an impact of injury within the one or more brain networks, and displaying a visualization of the determined impact of injury within the one or more brain networks or regions.

In one aspect, the method further comprises processing the first volumetric dataset to extract a first volumetric brain map for a first feature, and combining the first MRI data and the second MRI data is performed using the first volumetric brain map for the first feature.

In another aspect, the method further comprises processing the first MRI data to extract a second volumetric brain map for a second feature, and combining the first MRI data and the second MRI data is further performed using the second volumetric brain map for the second feature.

In another aspect, the first volumetric dataset comprises diffusion tensor imaging (DTI) data, the first feature is a first one selected from the group consisting of fractional anisotropy, radial diffusivity, mean diffusivity and axial diffusivity, and the second feature is a second one selected from the group consisting of fractional anisotropy, radial diffusivity, mean diffusivity and axial diffusivity.

In another aspect, the method further comprises transforming each of the first MRI data and the second MRI data into a common volumetric coordinate space, and combining the first MRI data and the second MRI data is performed using the transformed first MRI data and the transformed second MRI data.

In another aspect, the method further comprises applying a mask to the first MRI data and the second MRI, wherein the mask limits each of the first and second MRI data to voxels corresponding to a particular tissue type or anatomical region, and combining the first MRI data and the second MRI data is performed using the first MRI data and the second MRI data after the mask is applied.

In another aspect, the method further comprises normalizing at least some of the first MRI data to produce normalized first MRI data, and normalizing at least some of the second MRI data to produce normalized second MRI data, and combining the first MRI data and the second MRI data is performed using the normalized first MRI data and the normalized second MRI data.

In another aspect, normalizing at least some of the first MRI data and normalizing at least some of the second MRI data comprises using one or more of internal normalization, regional internal normalization and swapped regional internal normalization.

In another aspect, the method further comprises thresholding the normalized first MRI data to produce thresholded normalized first MRI data, and thresholding the normalized second MRI data to produce thresholded normalized second MRI data, and combining the first MRI data and the second MRI data is performed using the thresholded normalized first MRI data and the thresholded normalized second MRI data.

In another aspect, thresholding the normalized first MRI data comprises including in the thresholded normalized first MRI data only values that fall within two standard deviations from a mean value of the normalized first MRI data.

In another aspect, the method further comprises selecting a threshold value based, at least in part, on a type of MRI scan used to collect the first volumetric dataset and/or a neurological disease of the individual, and thresholding the normalized first MRI data comprises applying the selected threshold value to the normalized first MRI data to produce the thresholded normalized first MRI data.

In another aspect, combining on a voxel-by-voxel basis, the first MRI data and the second MRI data to produce a volumetric injury map comprises generating, for each voxel, a weighted combination of the first MRI data and the second MRI data.

In another aspect, the method further comprises selecting a first weighting factor based on a type of MRI scan used to collect the first volumetric dataset, selecting a second weighting factor based on a type of MRI scan used to collect the second volumetric dataset, and generating a weighted combination of the first MRI data and the second MRI data comprises combining the first MRI data weighted by the first weighting factor and the second MRI data weighted by the second weighting factor.

In another aspect, the first weighting factor and/or the second weighting factor are further selected based on a neurological disease of the individual.

In another aspect, generating a weighted combination of the first MRI data and the second MRI data for each voxel is based, at least in part, on a value of one or more other voxels in the first MRI data and/or the second MRI data.

In another aspect, the one or more other voxels include at least one voxel that neighbors the voxel for which the weighted combination is being generated.

In another aspect, generating a weighted combination of the first MRI data and the second MRI data for each voxel is based, at least in part, on a tissue type associated with the voxel.

In another aspect, the method further comprises applying a first weighting factor when the tissue type associated with the voxel is white matter, applying a second weighting factor when the tissue type associated with the voxel is grey matter.

In another aspect, performing a structural-functional analysis of one or more brain networks or regions by refining the volumetric injury map using a volumetric eloquence map comprises combining, on a voxel-by-voxel basis, the volumetric injury map and the volumetric eloquence map to produce an injury mask.

In another aspect, combining, on a voxel-by-voxel basis, the first MRI data and the second MRI data to produce a volumetric injury map and combining, on a voxel-by-voxel basis, the volumetric injury map and the volumetric eloquence map are merged into a single step.

In another aspect, performing a structural-functional analysis of one or more brain networks or regions further comprises comparing the injury mask to a library of masks, and determining the impact of the injury based on the comparison of the injury mask to the library of masks.

In another aspect, each mask in the library of masks indicates grey matter nodes and white matter tracts for a structural-functional unit in the brain, and determining the impact of the injury based on the comparison of the injury mask to the library of masks is further based on a spatial overlap between voxels in the injury mask and a structural-functional unit for a particular mask in the library of masks.

In another aspect, performing a structural-functional analysis of one or more brain networks or regions to determine an impact of injury within the one or more brain networks or regions comprises determining a location of voxels within the one or more brain networks or regions impacted by the injury.

In another aspect, performing a structural-functional analysis of one or more brain networks or regions to determine an impact of injury within the one or more brain networks or regions comprises determining a volume of the one or more brain networks or regions impacted by the injury.

In another aspect, the method further comprises estimating recoverability from the injury based, at least in part, on the structural-functional analysis and/or a tissue type.

In another aspect, performing a structural-functional analysis of one or more brain networks or regions by refining the volumetric injury map using a volumetric eloquence map comprises combining, on a voxel-by-voxel basis, the volumetric injury map and the volumetric eloquence map to produce an injury mask, and estimating recoverability from the injury comprises determining a proportion of voxels in the injury mask associated with white matter, and estimating the recoverability from the injury based on the determined proportion of voxels in the injury mask associated with white matter.

Some embodiments relate to a computer-implemented method or evaluating an impact of injury to brain networks or regions. The method comprises receiving magnetic resonance imaging (MRI) data of a brain of an individual, wherein the MRI data includes a first volumetric dataset recorded using first imaging parameters and a second volumetric dataset recorded using second imaging parameters, combining, on a voxel-by-voxel basis, first MRI data based on the first volumetric dataset and second MRI data based on the second volumetric dataset to produce a volumetric injury map, performing a structural-functional analysis of one or more brain networks or regions by refining the volumetric injury map using a volumetric eloquence map that specifies eloquent brain tissue within the one or more brain networks or regions to determine an impact of injury within the one or more brain networks or regions, and displaying a visualization of the determined impact of injury within the one or more brain networks or regions.

Some embodiments relate to a non-transitory computer-readable medium encoded with a plurality of instructions that, when executed, by at least one computer processor performs a method of evaluating an impact of injury to brain networks or regions. The method comprises receiving magnetic resonance imaging (MRI) data of a brain of an individual, wherein the MRI data includes a first volumetric dataset recorded using first imaging parameters and a second volumetric dataset recorded using second imaging parameters, combining, on a voxel-by-voxel basis, first MRI data based on the first volumetric dataset and second MRI data based on the second volumetric dataset to produce a volumetric injury map, performing a structural-functional analysis of one or more brain networks or regions by refining the volumetric injury map using a volumetric eloquence map that specifies eloquent brain tissue within the one or more brain networks or regions to determine an impact of injury within the one or more brain networks or regions, and displaying a visualization of the determined impact of injury within the one or more brain networks or regions.

Some embodiments are directed to techniques for combining multiple types of MRI data to evaluate, diagnose, stage and/or track the progress/recovery of a neurological disease or disorder, non-limiting examples of which include stroke, moyamoya disease, transient ischemic attack, concussion (mild traumatic brain injury (mTBI)), cumulative subconcussive impacts, chronic traumatic encephalography (CTE), Alzheimer's disease, dementia, and other neurological conditions.

Some embodiments are directed to combining two or more types of independently collected neuroimaging data (either in the same scan or different scan) to produce a composite image of a subject's injury. This composite image can be evaluated directly by a physician or can be compared to a reference library of neurological masks to determine the location, magnitude, recoverability and/or likely functional impact of an injury.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

BRIEF DESCRIPTION OF DRAWINGS

Various non-limiting embodiments of the technology will be described with reference to the following figures. It should be appreciated that the figures are not necessarily drawn to scale.

FIGS. 7A-C show an example of applying the processing techniques described herein to mild traumatic brain injury data;

DETAILED DESCRIPTION

The inventors have recognized and appreciated that some conventional techniques for evaluating injuries to the brain may be improved by combining magnetic resonance imaging (MRI) data that were recorded using different scanning parameters to determine an impact of an injury in a brain of an individual. Any type of MRI scan can be used in accordance with the techniques described herein. In particular, the techniques described herein can accommodate data that can be fit into a 3D-voxel based brain map (also referred to herein as a "volumetric dataset"). Non-limiting examples of different types of MRI data include any diffusion tensor imaging (DTI) metric, any functional magnetic resonance imaging (fMRI) data, any anatomical scan, grey matter volume, cortical thickness, resting cerebral blood flow (CBF), any kind of stimulated CBF, cerebrovascular reactivity (C V cineMRI, amplified MRI, or other data derived from an MRI acquisition. In some embodiments, imaging data collected using a modality other than MRI may be used and combined with MRI data using the techniques described herein. Non-limiting examples of non-MRI data include computed tomography (CT), positron emission tomography (PET), diffuse optical tomography, magnetoencephalography (MEG), functional near infrared spectroscopy, electroencephalography (EEG) and others.

Figure 1:
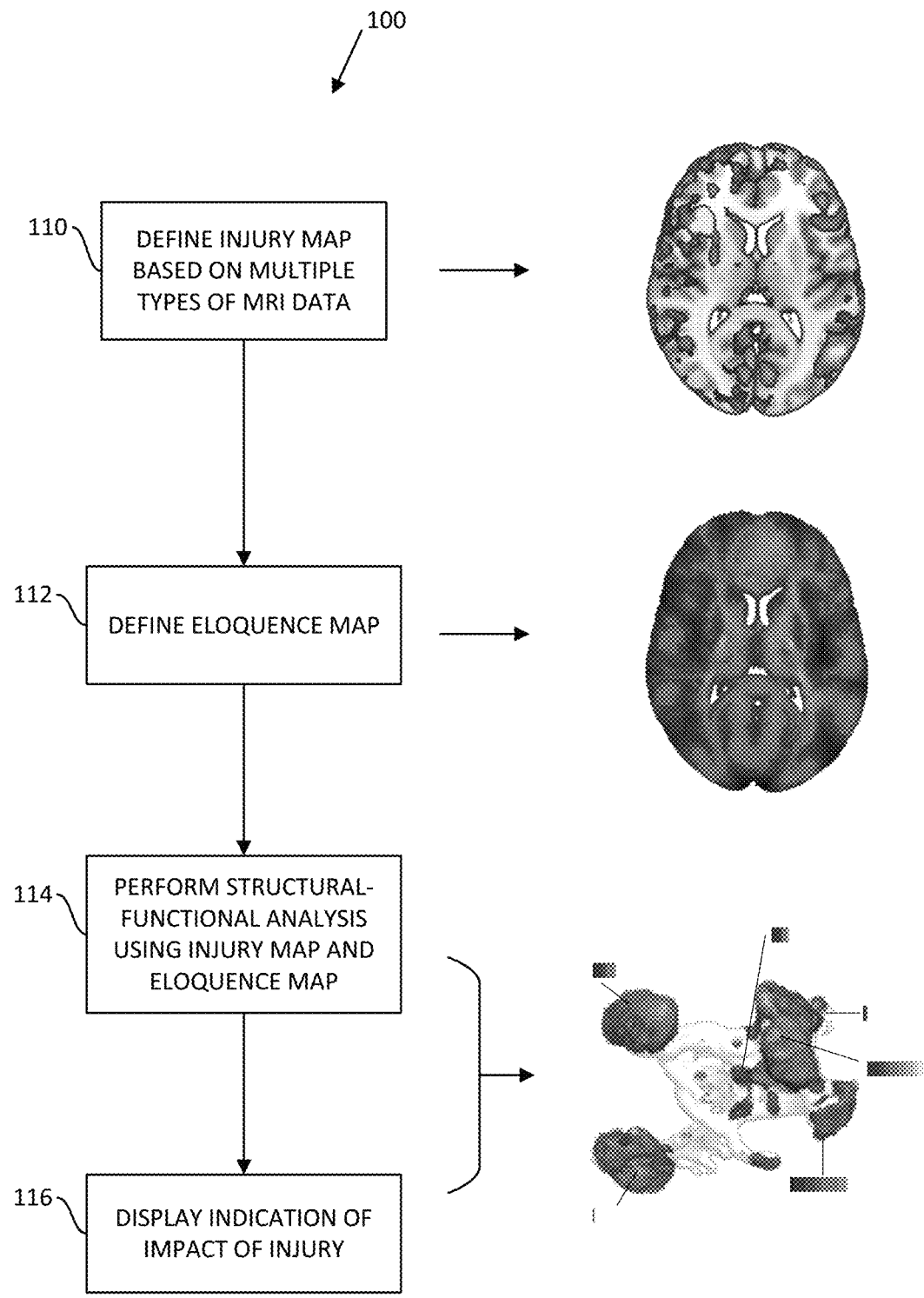
FIG. 1 is a flowchart of a process for determining an impact of a brain injury using multiple types of imaging data in accordance with some embodiments.

FIG. 1 illustrates a process 100 for evaluating a health of a subject and likely impacts of a brain injury in accordance with some embodiments. In act 110, an injury map for an individual is defined based on multiple types of MRI data (e.g., DTI data, CYR data, CBF data). In act 112, an eloquence map is defined. As discussed above, brain tissue includes both grey and white matter. While these tissues work in concert to perform all the brain's functions, not all regions of the grey and white matter are equally important. Processing and transmission centers responsible for critical tasks may be considered 'highly eloquent' whereas other regions not believed to have a function may be considered to be 'quiet' brain. Injury in the eloquent tissues of the brain tend to have a much greater behavioral impact than injury in quiet tissues. Within the eloquent tissue, a common misconception is that the brain is divided into large lobes that function independently. In reality, the brain relies on a series of distributed networks made up of small regions, or nodes, in the grey matter connected by white matter tracts. These networks combine and integrate the brain's specialized regions to perform complex tasks such as perception, reasoning, coordinated movements, memory and language. The eloquence reap defined in act 112 distinguishes eloquent regions of the brain from quiet regions of the brain. The eloquence map may be personalized for an individual or may be defined based on a group of individuals.

After defining an injury map in act 110 and an eloquence map in act 112, process 100 proceeds to act 114, where the injury map and the eloquence map are combined to perform a structural-functional analysis. For instance, a plurality of "structural-functional units" (SFUs), each of which represents a functional network of connected nodes in the brain that are activated together to perform various cognitive, sensory, motor, or sensorimotor tasks, may be defined. Examples of SFUs include, but are not limited to, a visuospatial network, a sensorimotor network, a default mode network, a working memory network, a salience network, an executive control network, a language network, and a motivation reward network. The structural-functional analysis performed in act 114 may, for example, evaluate the impact of injury within one or more SFUs by determining a percentage of volume of the SFU affected by the injury, a location of nodes within the SFU affected by the injury, the magnitude of impairment of locations within the SFU due to the injury, or using another suitable metric. Process 100 then proceeds to act 116, where an indication of the impact of the injury is displayed. The indication may take any suitable form, a non-limiting example of which is shown in FIG. 1 with further examples provided below. The displayed impact of the injury may be used, for example, to recommend behavioral exercises to facilitate recovery of the neural deficits, provide information to surgeons to guide brain surgery, to track the recovery of brain injury over time, or for any other suitable purpose.

Figure 2:
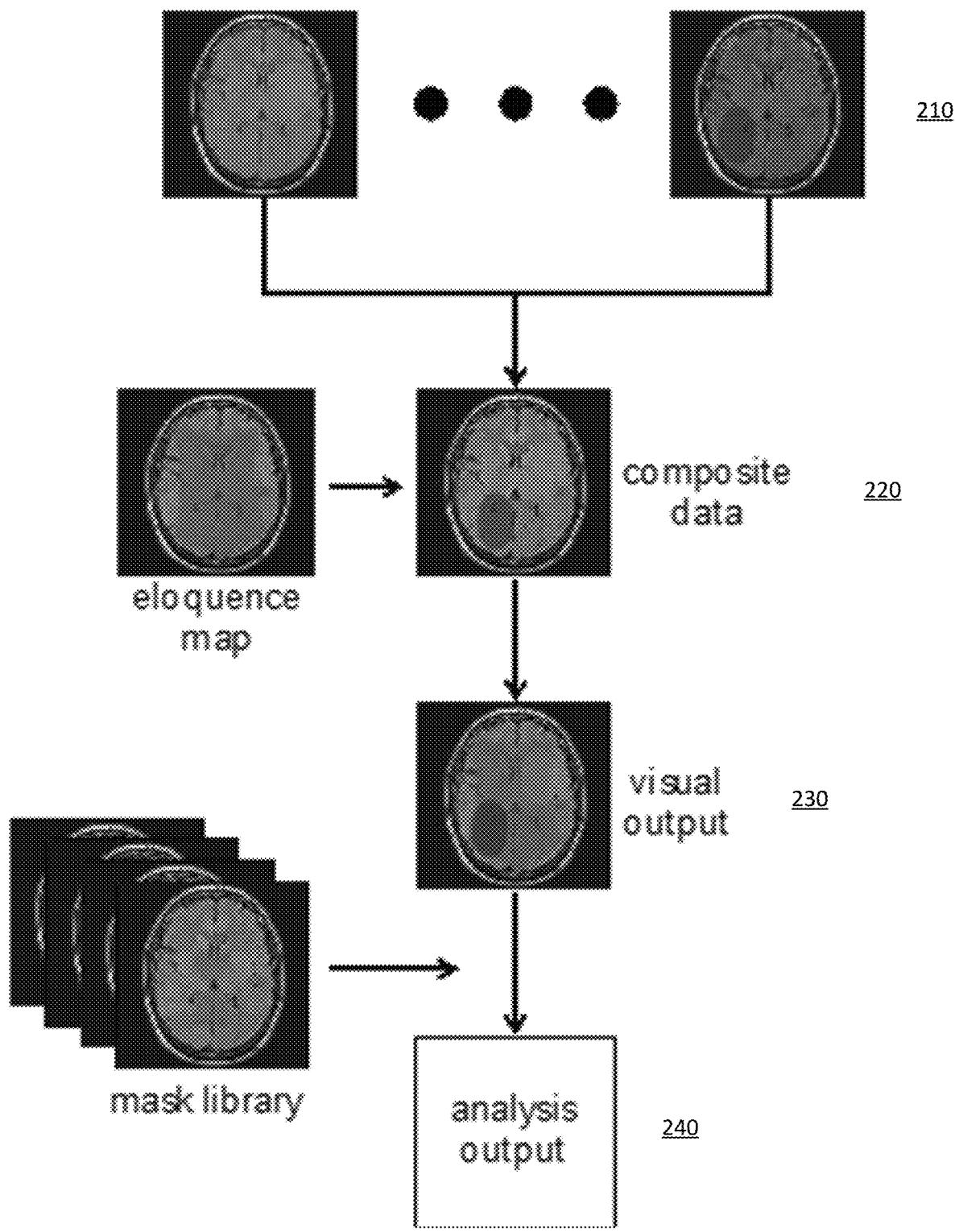
FIG. 2 is an alternate flowchart of a process for determining an impact of a brain injury using multiple types of imaging data in accordance with some embodiments.

FIG. 2 provides a further visualization of some of the steps in the processing pipeline of FIG. 1. In act 210, data having multiple data types is collected and processed. In act 220, the processed data is combined with eloquence map data to generate a composite image in which each voxel of the map is associated with a voxel of the eloquence map in addition to values for each type of data collected. At this step, an injury mask for the subject may also be generated. In act 230, visual output based on the injury mask may be displayed to a physician or other user. In act. 240, the injury mask data may be compared against reference data to provide additional information about the subject's injury, examples of which are discussed in more detail below.

Figure 3:
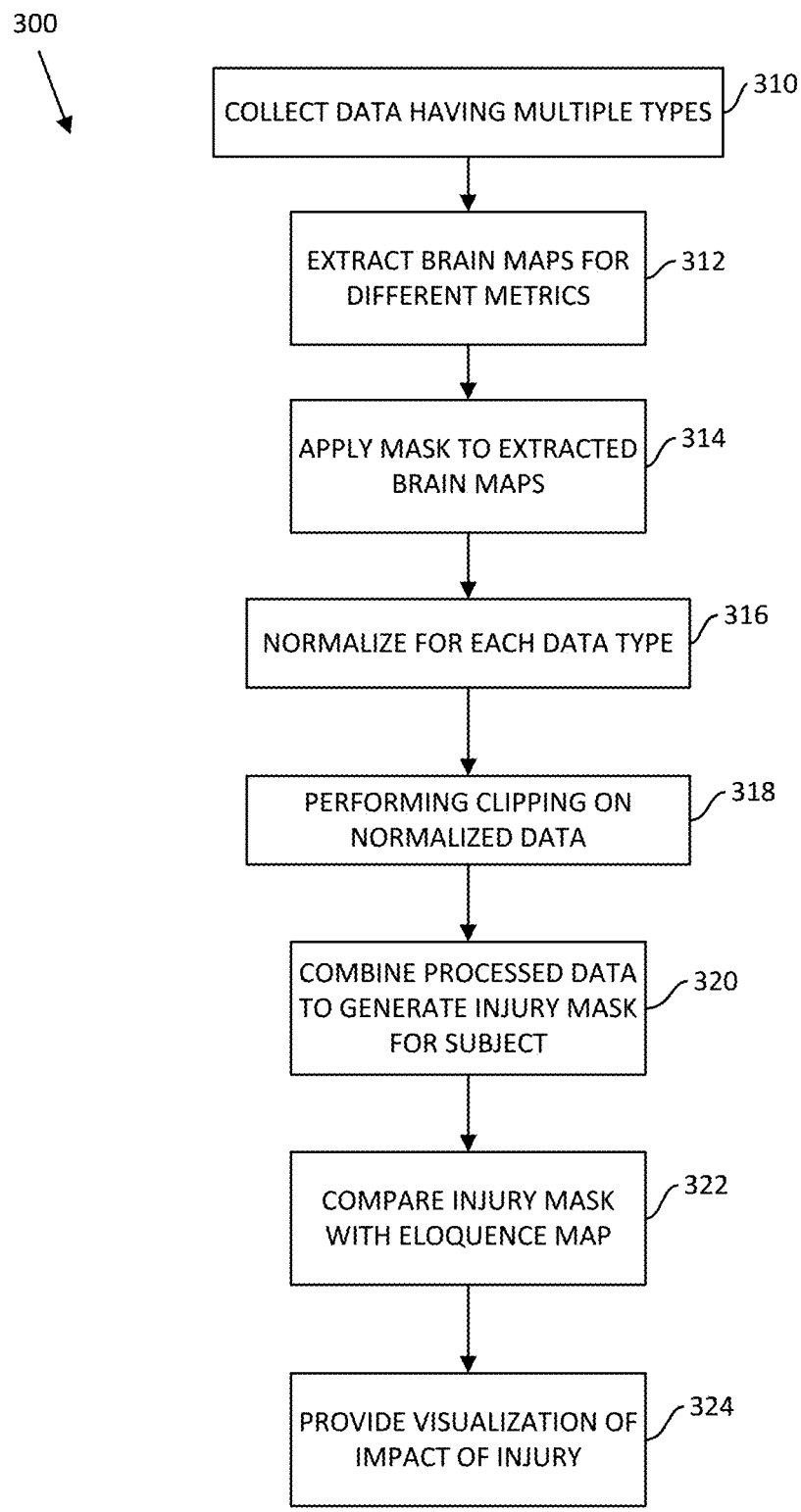
FIG. 3 is a detailed flowchart of a process for determining an impact of a brain injury using multiple types of imaging data in accordance with some embodiments.

FIG. 3 illustrates a detailed process 300, in which several acts of process 100 are expanded to show additional acts that may be included in some embodiments. In act 310, volumetric datasets (e.g., MRI data) having different data types are collected and the raw imaging data may be processed (e.g., filtered, amplified, etc.). Rather than, or in addition to using the processed raw data for further analysis, in some embodiments, process 300 proceeds to act 312, where additional brain maps (e.g., volumetric datasets) corresponding to particular imaging features or metrics are generated from the processed raw data. For example, from diffusion tensor images, different metrics (e.g., fractional anisotropy (FA), radial diffusivity (RD), mean diffusivity (MD), axial diffusivity (AD)) may be extracted to produce volumetric feature-based brain maps in which the value for each voxel represents a value for the particular feature or metric. Once the feature-based brain maps are extracted, process 300 proceeds to act 314, where a mask may be applied to the processed data to limit the available data to a particular tissue type (e.g., white matter, grey matter) or anatomical region. For instance, the processed data may be masked to limit the data based on tissue type, e.g., limiting DTI data to only white matter tracts. In other embodiments, a mask may be applied to limit the data in other ways, for example, based on anatomy. For example, the data may be limited to only a specific white matter tract for a highly focused analysis of that tract.

To enable combination of datasets that may have been collected across different scans, the masked feature-based data maps may then be transformed into a standard coordinate space (e.g., using a standard space atlas). In some embodiments, a publically-available standard space atlas (e.g., the Montreal Neurological institute (MN') atlas) may be used. Alternatively, a custom atlas may be used, and all of the data (e.g., the current subject's data and any reference subject's data) may be transformed into the same coordinate space.

The process then proceeds to act 316, where the individual data types (e.g., data for each of the metrics/features of interest) are normalized. Normalization establishes a mean and standard deviation (measure of central tendency and defined distribution) for the values in the data and applies a Z-score (or other statistical measure of difference) to determine how far an individual data point falls from the mean. Normalization may be performed in any suitable way, examples of which are described in more detail below.

Normalize against a reference population (e.g., healthy, age and sex-matched subjects). The mean and standard deviation for a particular voxel is determined from a group (e.g., 20 or more) of comparable, healthy individuals.

Internal normalization: the global mean/standard deviation for a data type is determined within the subject. The internal normalization approach is intended to account for subjects who have some baseline depression or elevation in their neurological state at the time of their scan. Example: an elite athlete ran from the train station to the scan location immediately before his scan.

Regional internal normalization. Local mean/standard deviation is determined using regional boundaries. In one example, normalization may be performed in different zones of the brain supplied by different cerebral arteries. This is an additional to check to ensure a larger lesion hasn't skewed the internal normalization process.

Swapped regional internal normalization. Regionally-defined mean/standard deviations determined using regional internal normalization are rotated/swapped.

Process 300 then proceeds to act 318, where the normalized data for a subject is clipped. In some embodiments, clipping the normalized data may involve removing values surrounding the mean. For example in cerebrovascular reactivity (CVR) MRI, data may be clipped such that only regions with values+/−2 standard deviations away from the mean would remain in the analyzed dataset. In other embodiments, clipping the normalized data involves including in the analyzed data, only values that are above or below a threshold, for example, by setting all other values in the map to 'not a number' (NaN). The threshold for clipping data may be selected, for example, based on the scan type (e.g., MRI scan parameters) and/or the neurological disease of the subject. An intention of clipping the data in this manner is that a healthy individual would show no signal remaining in their brain maps after the threshold is applied while a non-healthy subject would show only display signal related to their injury/condition.

Process 300 then proceeds to act 320, where the processed (e.g., clipped) data is combined into a multi-channel composite image or volume. In a multi-channel arrangement the different data types are layered into the same standard space atlas (e.g., the MNI atlas or another standard space). In some embodiments, each voxel in the composite volume is represented by a series of data slots (a, b, c, d, etc. . . . ), with each data type (metric) occupying the same data slot across the brain (DTI-FA, DTI-RD, CVR, CBF, fMRI . . . ).

In other embodiments, each of the voxels in the composite volume represents a single value as a weighted average of each of the processed data maps to produce an injury map for of a subject's brain. The weighting may be determined in any suitable way. In some embodiments, the weighting may be based, at least in part, on a neurological disease of the subject, with each of a plurality of neurological diseases being associated with a disease-specific weighting algorithm. Processing the same data with different weighting algorithms may result in the production of more than one injury map for the subject. In some embodiments, weighting factors applied to the different datasets may be determined based, at least in part, on the different data types. For example, when evaluating mild Traumatic Brain Injury (mTBI) low cerebral blood flow (CBF) may be weighted more strongly than other data types. In some embodiments, inclusion factors may also be used to determine the weighting. For example, when evaluating stroke, low grey matter volume (GMV) may only be considered if it is accompanied by low CBE In some embodiments, information about values of other voxels in the composite volume may be used. For instance, proximity may be used when weighting data types. As an example, reduced fractional anisotropy (FA) in white matter voxels proximal to voxels with low CBF or low cerebrovascular reactivity (CYR) may be more important than low FA on its own. In some embodiments, a continuity threshold may be used, in which injured voxels must be connected to be included Using a continuity threshold limits noise in the injury map. In yet further embodiments, injury in different tissue types (e.g., white matter vs. grey matter) may be weighted differently.

Figure 4:
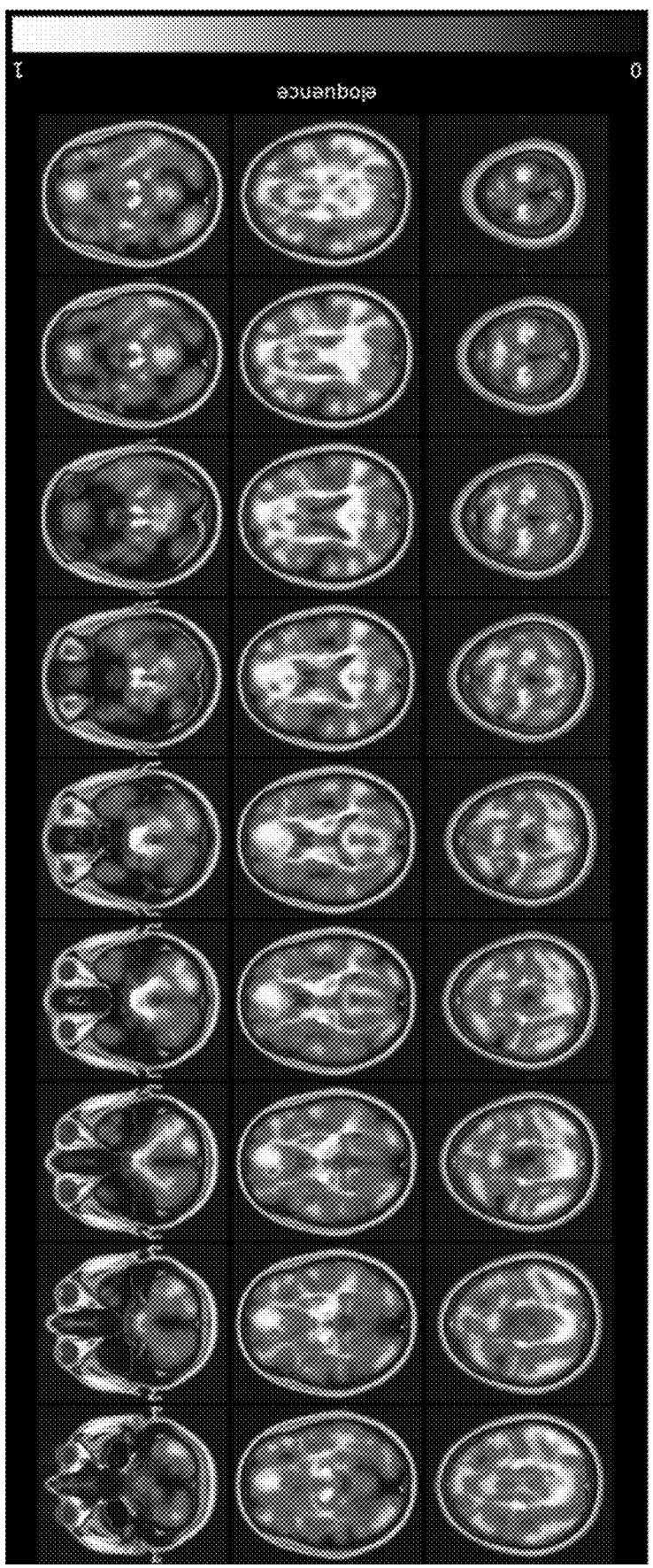
FIG. 4 shows examples of eloquence maps that may be used in determining an impact of a brain injury in accordance with some embodiments.

In addition to the data types, in some embodiments, an eloquence map can also be layered into one of the channels in the composite image. As discussed briefly above, an eloquence map is a 3D voxel-wise representation of the brain (e.g., in a standard space atlas) that contains a probability that a given voxel resides in eloquent brain tissue. Eloquent brain tissue represents the regions of the brain that are most functionally or cognitively relevant. The brain has regions that range from 100% to 0% eloquent. FIG. 4 shows an example of an eloquence map that may be used in accordance with some embodiments. In other embodiments, the injury map for the subject is compared with the eloquence map in act 322 as described in more detail below.

In a multiple normalization scheme, several versions of a composite may be made for a subject in act 320 by making different combinations of the normalization approaches for each data type.

Composite brain maps may be processed using a function that combines the values in each data type (accounting for the polarity if required) to output a singular intensity value/voxel that represents all the data types present.

The process then proceeds to act 322, where the injury mask is compared with an eloquence map to determine if injured tissue falls within eloquent tissue and is expected to impact behavior. Dice coefficients (or other comparative metric) may be used to indicate the extent of overlap between the injury mask and the eloquence map. An algorithm may be applied to determine the location, magnitude, recoverability and likely functional impact of an injury. The injury may be localized to specific functions regions/networks/functional zone using specific sub-eloquence maps. For instance, the comparison of the injury mask and the eloquence map may be used determine the proportion and/or magnitude of 'activated' voxels in a particular structural-functional network (e.g., a structural functional unit) to indicate/anticipate the impact of injury's effect.

Location of the injury: may be determined by the localized presence of data values outside the normal range for healthy, comparable subjects. In some embodiments, this analysis may apply to all data types except resting state (RS) connectivity. RS alterations tend to indicate an injury but the effect is more distributed.

Magnitude of the injury: may be determined by the total number/volume of effected voxels and intensity of the data outside the normal range.

Likely functional impact of an injury: may be determined by comparing the injury mask to a library of masks indicating the grey matter nodes and white matter tracts for different structural-functional units in the brain. If an injury mask has overlap with a particular SFU then it may be inferred that the subject is likely to be impaired in those functions.

Recoverability: functional losses due to a lesion in the white matter may be less likely to recover than lesions in the grey matter. Recovery may be determined by screening the injury mask against a reference library of white matter tracts. In some embodiments, the reference masks are generated based on a database of collected subject data.

Process 300 then proceeds to act 324, where a visualization of the impact of the injury is output to a viewer. The visualization may be provided on a user interface to enable, for example, a physician or radiologist to evaluate the extent of the injury and facilitate medical care. A user may interact with the user interface to select views from a variety of options including, but not limited to, the type of normalization for each data type, population normalized against for each data type, the level and direction of thresholding for each data type. A user may also interact with the user interface to view individual data layers or add layers as required (using the requested settings). Color options may be available for different data types. The physician/user may use this visual output indicating the location and magnitude of a subject's injury to make a diagnosis, provide a rehabilitation recommendation, or provide treatment.

Figure 5:
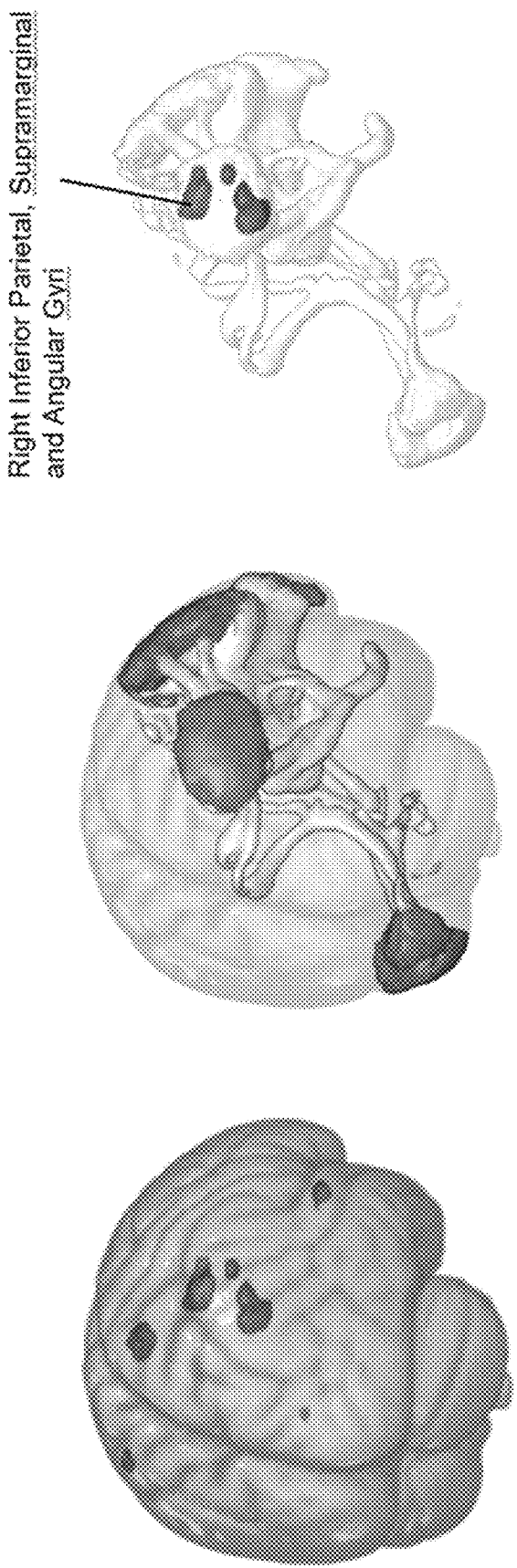
FIGS. 5A-C show an example of applying the processing techniques described herein to stroke data.

FIGS. 5A-C show examples of visualizations generated by applying the techniques described herein to an individual who suffered a stroke. FIG. 5A shows an injury map for the individual generated by combining multiple types of MRI data including grey matter volume (GMV) data, cerebral blood flow (CBF) data, and diffusion tensor imaging (DTI) data. FIG. 5B shows an eloquence map for a right executive control network having grey matter nodes and white matter tracts connecting the nodes. As shown, the eloquence map highlights regions of the brain that include eloquent tissue within this network. FIG. 5C shows a display of an impact of the individual's injury on the right executive control network shown in FIG. 5B using the techniques described herein. For instance, structural-functional analysis was used to combine the injury map shown in FIG. 5A with the eloquence map shown in FIG. 5B to determine that the individual's injury (stroke lesion) impacted a 4.6% volume of the right executive control network. Particular locations within the network most impacted by the stroke lesion are also identified. Such analysis may be useful to guide rehabilitation treatment for the individual by focusing on rehabilitation options targeted to remediating those areas of the brain most affected by the injury.

Figure 6:
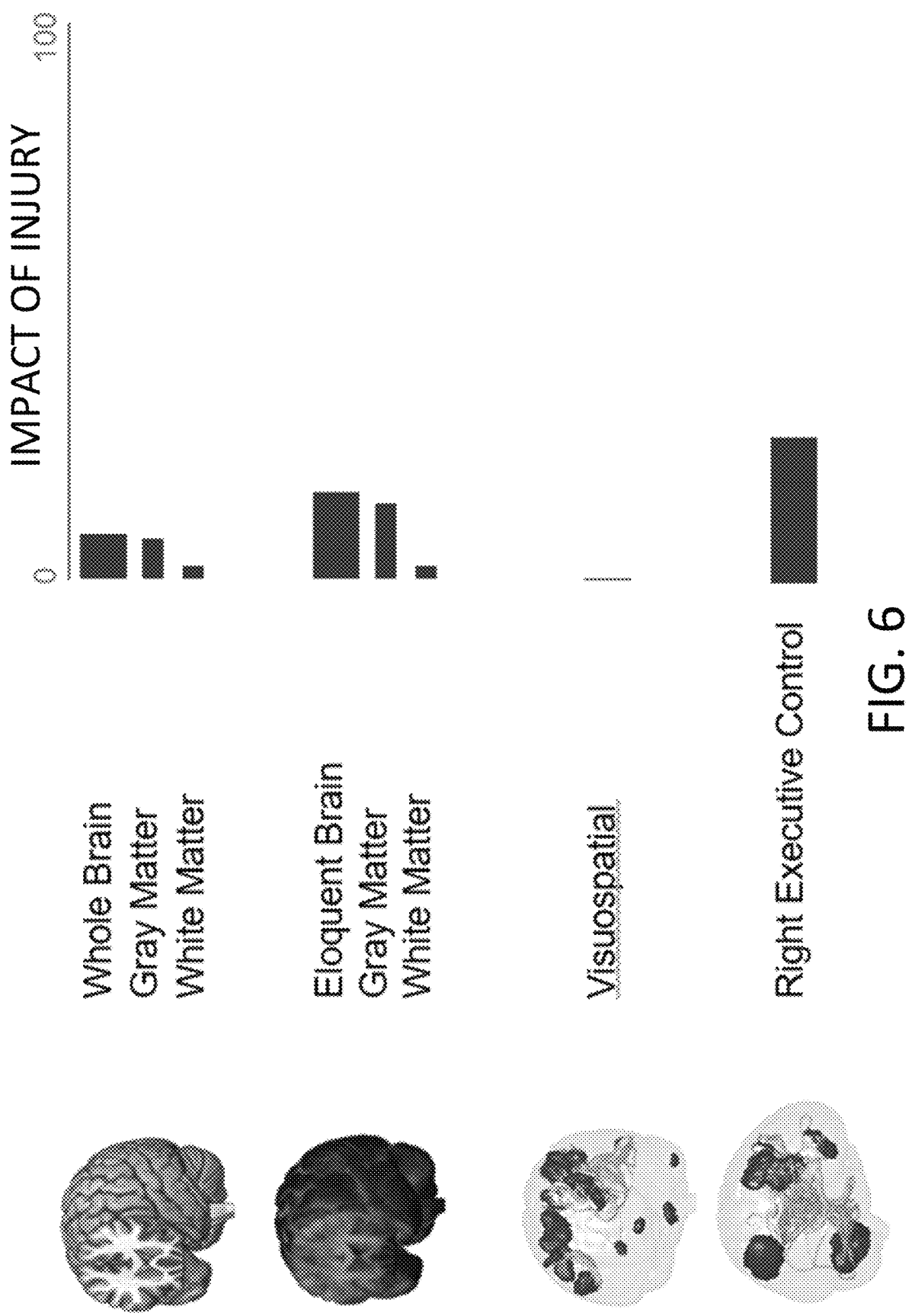
FIG. 6 is a plot that shows the proportion of various brain networks affected by injury as determined using techniques in accordance with some embodiments.

FIG. 6 shows an additional visualization of the impact of a stroke lesion on multiple brain networks as determined using the techniques described herein. For each of the brain networks, an impact of the injury on a scale from 0 (least impacted) to 100 (most impacted) is shown. For instance, for this particular stroke lesion, grey matter is impacted more than white matter in both the whole brain analysis and an analysis of eloquent tissue. Additionally, FIG. 6 shows that the right executive control network is impacted substantially more than the visuospatial network, thereby suggesting that therapies directed to improving executive control are likely to be more effective than those targeting visuospatial improvements in treating this particular patient. The analyses described herein thereby allow for guiding personalized rehabilitation options based on an individual's specific injury profile.

FIGS. 7A-C show examples of visualizations generated by applying the techniques described herein to an individual who experienced mild traumatic brain injury (mTBI). 7A shows an injury map for the individual generated by combining multiple types of MRI data including grey matter volume (GMV) data, cerebral blood flow (CBF) data, cerebrovascular reactivity (CVR) data, and diffusion tensor imaging (DTI) data. FIG. 7B shows an eloquence map for a right executive control network having grey matter nodes and white matter tracts connecting the nodes. As shown, the eloquence map highlights regions of the brain that include eloquent tissue within this network. FIG. 7C shows a display of an impact of the individual's injury on the right executive control network shown in FIG. 7B using the techniques described herein. For instance, structural-functional analysis was used to combine the injury map shown in FIG. 7A with the eloquence map shown in FIG. 7B to determine that the individual's injury impacted the grey matter within the network more than the white matter within the network. Particular locations within the network most impacted by the injury are also identified.

Figure 8A:
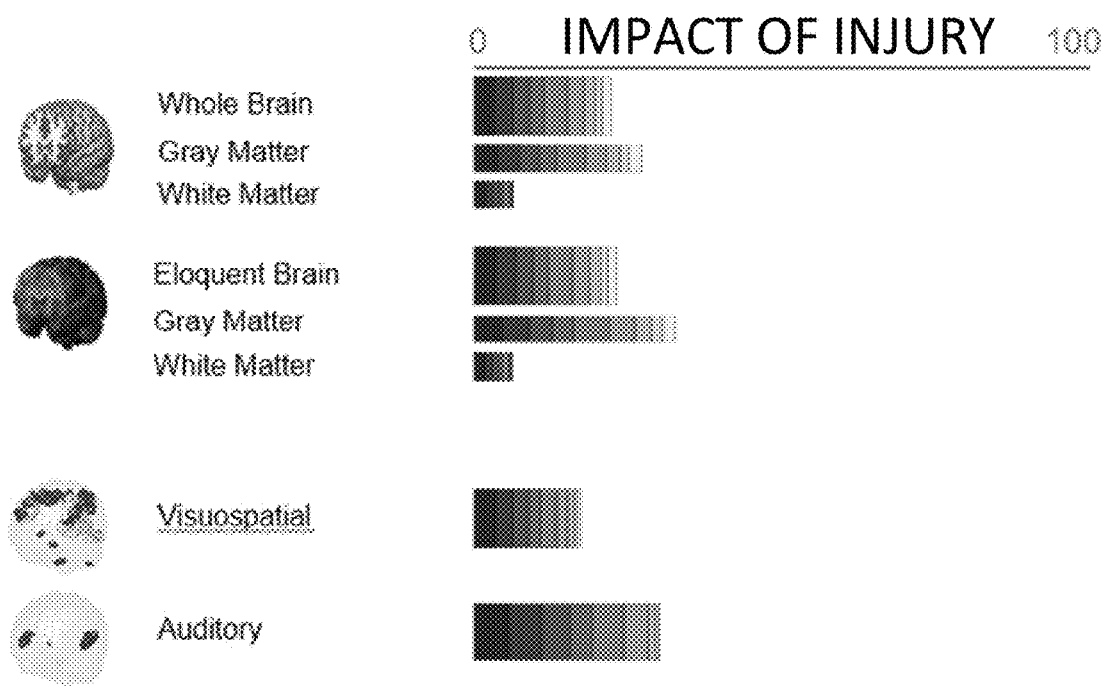
FIGS. 8A and 8B show example displays for evaluating the impact of injury across the brain in accordance with some embodiments.
Figure 8B:
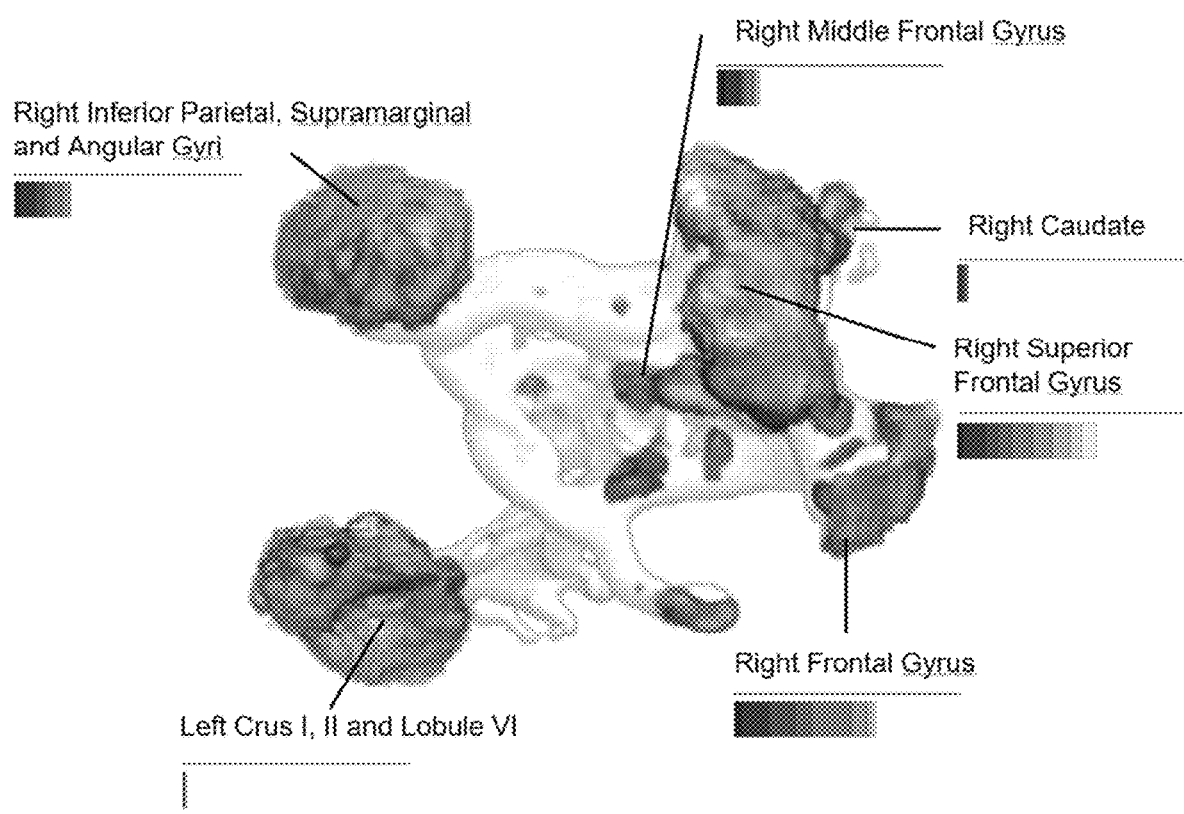

FIGS. 8A and 8B show additional visualization of the impact of an mTBI injury on multiple brain networks as determined using the techniques described herein. As shown in FIG. 8A, for each of the brain networks, an impact of the injury on a scale from 0 (least impacted) to 100 (most impacted) is shown. For instance, for this particular injury, grey matter is impacted more than white matter in both the whole brain analysis and an analysis of eloquent tissue. Additionally, FIG. 8A shows that the auditory network is impacted more than the visuospatial network, thereby suggesting that therapies directed to improving audio processing are likely to be more effective than those targeting visuospatial improvements in treating this particular patient. As shown, the visualization in FIG. 8A includes both an analysis of the impact of the injury in each of multiple networks (on a scale of 0-100), but also magnitude information about the impact of the injury within each network (shown by the different shaded bars. It should be appreciated that the visualization shown in FIG. 8A is merely one way of displaying the impact of injury data determined using the techniques described herein and other types of visualization are also possible.

FIG. 8B shows an additional visualization of the impact of a mTBI injury on the right executive control network shown in FIG. 7B. The visualization in FIG. 8B displays further detail about the impact of the injury in particular nodes of the network. For instance, FIG. 8B shows the impact of injury to be highest in the right superior frontal gyrus and the right frontal gyrus nodes of the executive control network, thereby suggesting that treatment targeted on improving function in these areas may be beneficial to this particular individual.

Figure 9:
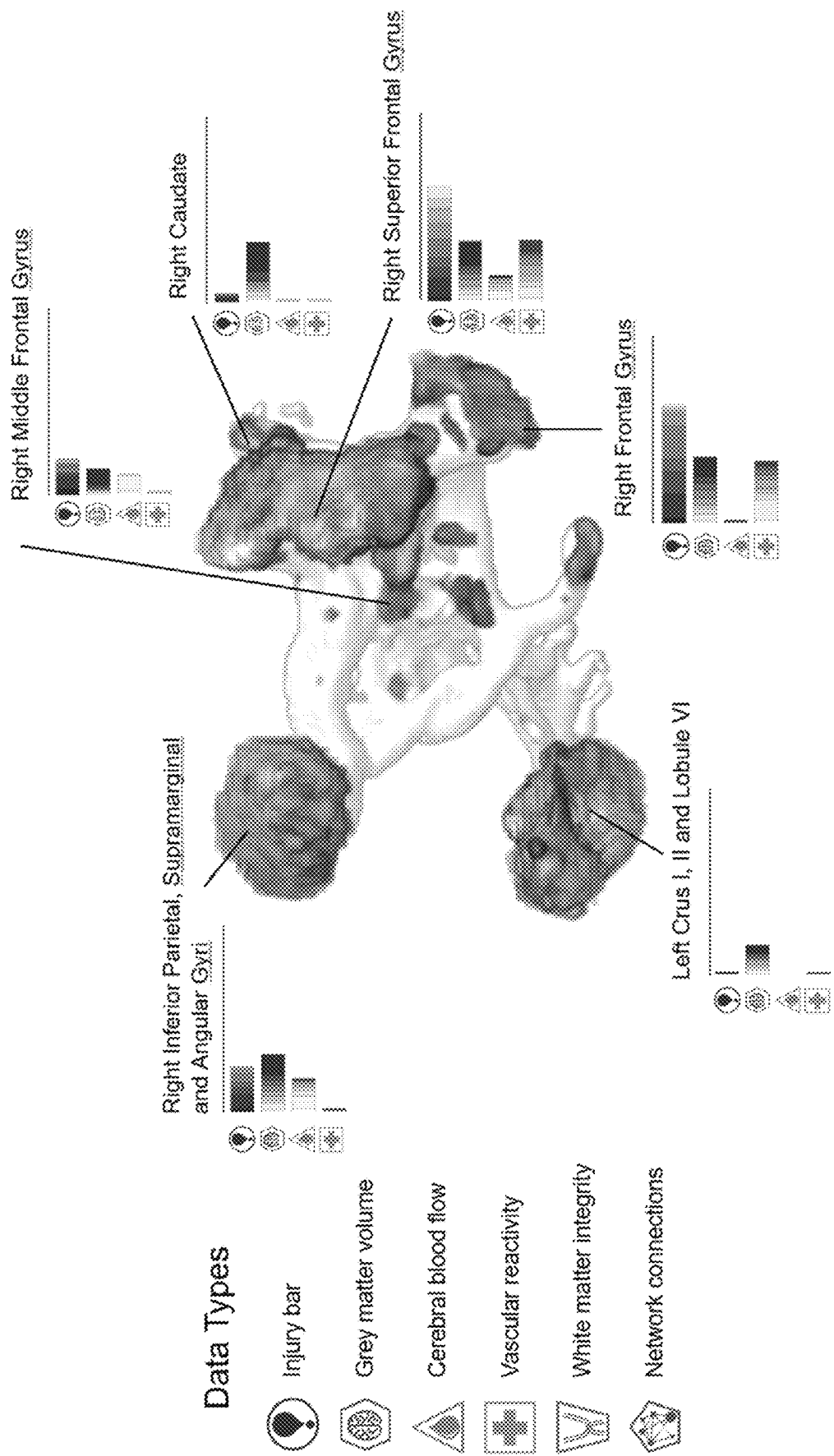
FIG. 9 shows an example display with overlays for different component data determined in accordance with some embodiments.

FIG. 9 shows yet another visualization generated based on the techniques described herein. The visualization shown in FIG. 9 is similar to the visualization in FIG. 8B and provides additional detail about the relative impact of each of the imaging data types that contributed to the injury mask for each of the nodes in the right executive control network. For instance, in the right superior frontal gyrus, the grey matter volume (GMV) and cerebrovascular reactivity (CVR) contributed most to the impact of the injury, whereas for the right inferior parietal, supramarginal and angular gyrus node, grey matter volume (GMV) and cerebral blood flow (CBF) contributed most of the impact of the injury.

Any suitable imaging data types, including not limited to those described above, may be used. Some examples of imaging data types include:

Structural Organization (grey matter): The grey matter is highly organized in functionally distinct regions. The volume of a given region has been correlated with an individual's performance in a related behavior. Larger volumes have been associated with greater capability while smaller volumes can indicate injury or disease and generally reduced performance. Each of the brain's tissue types (e.g., white matter and grey matter) respond differently within the scanner's magnetic field in an anatomical scan and thus, show up differently on the images. The resulting contrast allows for segmenting the brain's features and determine the regional volume of grey matter throughout the cortex.

Structural Connections (white matter): The other major structural aspect of the brain is the white matter. In healthy white matter, the bundles of axons are highly organized and well insulted with myelin. These aspects can be evaluated by measuring the direction of water diffusion in the white matter tracts using Diffusion Tensor Imaging (DTI). The membranes that make up each axon only permit water to flow along the length of tract resulting in highly directional diffusion. An injury or disease can disrupt integrity of the axons altering the water's diffusion path. The techniques described herein may evaluate the direction of diffusion within each voxel to create a map of the overall health of the tracts and identify any areas of concern.

Functional Connections: As discussed above, the brain's grey matter is organized into distributed functional networks. The function of each of these networks may be evaluated using the techniques described herein by measuring how well the activation of the nodes is synchronized. The function can be determined by measuring small changes in oxygen consumption throughout the grey matter. A local increase of oxygen consumption indicates activation of that group of neurons. By comparing the patterns of fluctuation over time between two regions, how well those regions are working together or share a functional connection can be measured. Alteration or loss of functional connection can be an indicator of injury or disease.

Physiology-Blood Flow: For the brain to perform at its best, it requires a healthy supply of blood. Blood delivers the oxygen, energy and other nutrients necessary for the brain to perform all its various functions. To measure blood flow, arterial spin labeling (ASL) may be used. During ASL, protons in the blood flowing into the brain are magnetically labeled to act as an endogenous tracer. Using MRI, the movement of the magnetized blood throughout the head can be tracked to measure its flow. This measurement allows for generation of a map of the average flow to identify areas of high or low flow. Small or local increases or decreases in blood flow can impact the ability of that region to functional normally and can indicate injury or disease.

Physiology-Cerebrovascular Reactivity: Blood flow to the brain is highly regulated. It responds continuously to changes in blood pressure, arterial gases, neural activity, etc., to maintain homeostasis. In particular, the blood vessels in the brain, or the cerebrovasculature, are very sensitive to changes in the partial pressure of arterial carbon dioxide ($PaCO_2$). Elevated $PaCO_2$, also known as hypercapnia, causes vessels to dilate resulting in increased cerebral blood flow. Measuring the change in flow during hypercapnia can provide an indication of cerebrovascular reactivity (CVR) and can identify regions with impaired vascular function. Assessing CVR provides an indication of vascular health or metabolic distress in the tissue.

Figure 10:
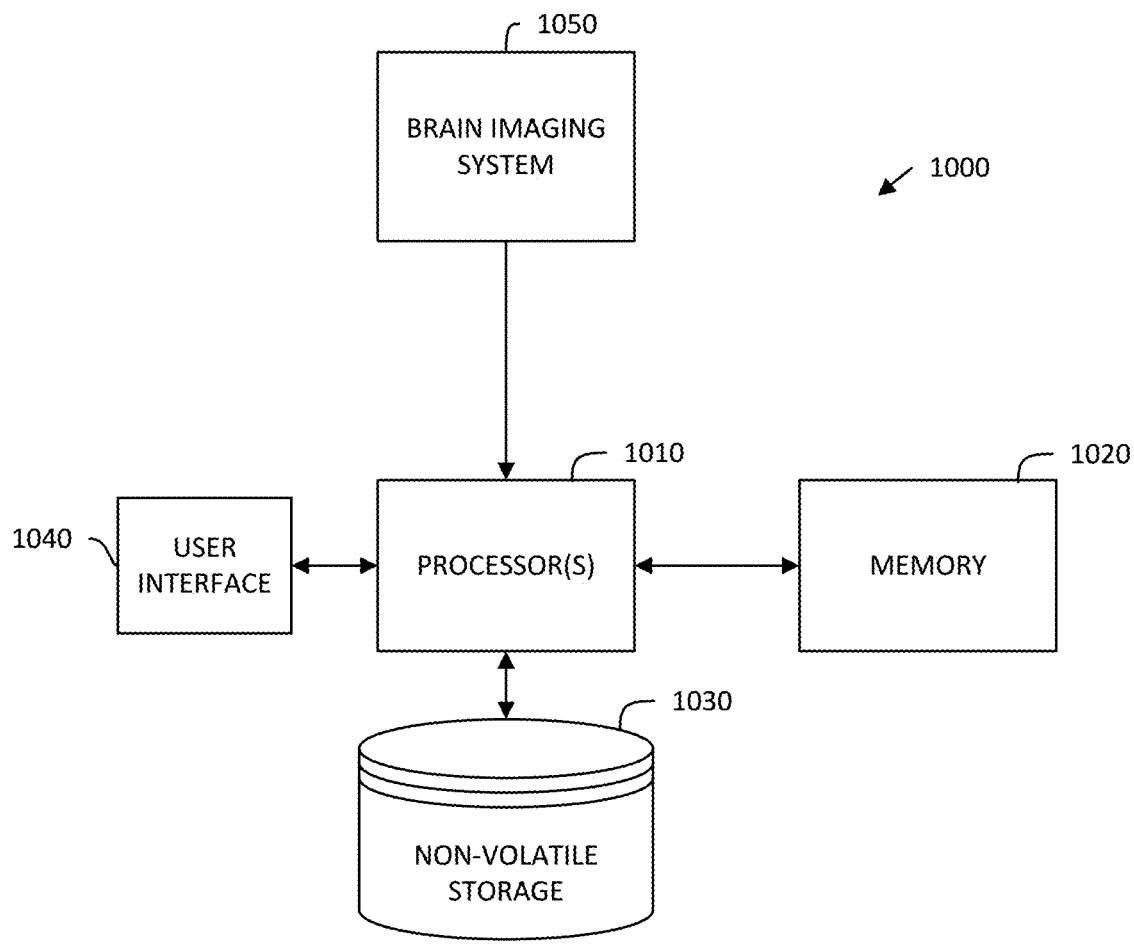
FIG. 10 is a block diagram of a computer system on which some embodiments may be implemented.

An illustrative implementation of a computer system 1000 that may be used in connection with any of the embodiments of the disclosure provided herein is shown in FIG. 10. The computer system 1000 includes one or more computer hardware processors 1010 and one or more articles of manufacture that comprise non-transitory computer-readable storage media (e.g., memory 1020 and one or more non-volatile storage devices 1030). The processor(s) 1010 may control writing data to and reading data from the memory 1020 and the non-volatile storage device(s) 1030 in any suitable manner.

To perform any of the functionality described herein, the processor(s) 1010 may execute one or more processor executable instructions stored in one or more non-transitory computer-readable storage media (e.g., the memory 1020), which may serve as non-transitory computer-readable storage media storing processor-executable instructions for execution by the processor(s) 1010.

In some embodiments, computer system 1000 also includes a brain imaging system (e.g., an MRI system) 1050 that provides brain imaging data to processor(s) 1010. Brain imaging system 1050 may be communicatively coupled to processor(s) 1010 using one or more wired or wireless communication networks. In some embodiments, processor(s) 1010 may be integrated with the brain imaging system in an integrated device. For example, processor(s) 1010 may be implemented on a chip arranged within a device that also includes brain imaging system 1050.

Brain imaging system 1050 may be configured to perform brain imaging on an individual to obtain brain data using different imaging parameters (e.g., to obtain different types of imaging data). The brain imaging data determined from the brain imaging system 1050 may then be provided to the processor(s) 1010 for inclusion in an injury detection and analysis, as described above.

In some embodiments, computer system 1000 also includes a user interface 1040 in communication with processor(s) 1010. The user interface 1040 may be configured to display one or more visualizations of an impact of an injury, examples of which are described above. User interface may also be configured to provide a treatment recommendation determined based, at least in part, on the techniques described herein. In some embodiments, the user interface is interactive by enabling a user (e.g., a physician or other healthcare provider) the ability to view different overlays or brain networks in response to interacting with the user interface.

An additional application for this process (in part or in whole) is to be an evaluation measure for many neurological clinical trials. A significant issue in the design and analysis of stroke trials is the elevated variance in functional outcomes due to heterogeneity in the location of a stroke. The techniques described herein can be used to standardize functional outcome for the purposes of evaluating a stroke intervention during a clinical trial and the prediction of functional deficits in trials or direct patient care. This concept can be applied to any other neurodegenerative disease.

In some implementations, the eloquence map can be used as a tool for neurosurgical guidance. For example, the eloquence map can be used to develop and modify a surgical plan with predictions of how likely a patient is to have lasting cognitive impairment by following one plan or another during an intervention. The eloquence map may be used in conjunction with an existing platform to surgical and radiosurgical planning and or guidance.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as one or more controllers that control the above-discussed functions. The one or more controllers can be implemented in numerous ways, such as with dedicated hardware or with one or more processors programmed using microcode or software to perform the functions recited above.

In this respect, it should be appreciated that one implementation of the embodiments of the present invention comprises at least one non-transitory computer-readable storage medium (e.g., a computer memory, a portable memory, a compact disk, etc.) encoded with a computer program (i.e., a plurality of instructions), which, when executed on a processor, performs the above-discussed functions of the embodiments of the present invention. The computer-readable storage medium can be transportable such that the program stored thereon can be loaded onto any computer resource to implement the aspects of the present invention discussed herein. In addition, it should be appreciated that the reference to a computer program which, when executed, performs the above-discussed functions, is not limited to an application program running on a host computer. Rather, the term computer program is used herein in a generic sense to reference any type of computer code (e.g., software or microcode) that cart be employed to program a processor to implement the above-discussed aspects of the present invention.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of which an example has been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc., in the claims to modify a claim element does not by itself connote any priority, precedence, or order of one claim element over another or the temporal order in which acts of a method are performed. Such terms are used merely as labels to distinguish one claim element having a certain name from another element having a same name (but for use of the ordinal term).

The phraseology and terminology used herein is for the purpose of description and should not be regarded as limiting. The use of "including," "comprising," "having," "containing," "involving," and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting. The invention is limited only as defined by the following claims and the equivalents thereto.

What is claimed is:

1. A computerized system for evaluating an impact of injury to brain networks or regions, the system comprising:
at least one computer processor; and
at least one computer-readable medium encoded with a plurality of instructions that, when executed by the at least one computer processor, perform a method of evaluating an impact of injury to one or more brain networks or regions, the method comprising:
receiving magnetic resonance imaging (MRI) data of a brain of an individual, wherein the MRI data includes a first volumetric dataset recorded using first imaging parameters and a second volumetric dataset recorded using second imaging parameters;
combining, on a voxel-by-voxel basis, first MRI data based on the first volumetric dataset and second MRI data based on the second volumetric dataset to produce a volumetric injury map;
performing a structural-functional analysis of one or more brain networks or regions by refining the volumetric injury map using a volumetric eloquence map that specifies eloquent brain tissue within the one or more brain networks or regions to determine an impact of injury within the one or more brain networks; and displaying a visualization of the determined impact of injury within the one or more brain networks or regions.

2. The computerized system of claim 1, wherein the method further comprises:

processing the first volumetric dataset to extract a first volumetric brain map for a first feature, and wherein combining the first MRI data and the second MRI data is performed using the first volumetric brain map for the first feature.

3. The computerized system of claim 2, wherein the method further comprises:

processing the first MRI data to extract a second volumetric brain map for a second feature, and wherein combining the first MRI data and the second MRI data is further performed using the second volumetric brain map for the second feature.

4. The computerized system of claim 3, wherein the first volumetric dataset comprises diffusion tensor imaging (DTI) data, the first feature is a first one selected from the group consisting of fractional anisotropy, radial diffusivity, mean diffusivity and axial diffusivity, and the second feature is a second one selected from the group consisting of fractional anisotropy, radial diffusivity, mean diffusivity and axial diffusivity.

5. The computerized system of claim 1, wherein the method further comprises:

transforming each of the first MRI data and the second MRI data into a common volumetric coordinate space, and wherein combining the first MRI data and the second MRI data is performed using the transformed first MRI data and the transformed second MRI data.

6. The computerized system of claim 1, wherein the method further comprises:

applying a mask to the first MRI data and the second MRI, wherein the mask limits each of the first and second MRI data to voxels corresponding to a particular tissue type or anatomical region, and wherein combining the first MRI data and the second MRI data is performed using the first MRI data and the second MRI data after the mask is applied.

7. The computerized system of claim 1, wherein the method further comprises:

normalizing at least some of the first MRI data to produce normalized first MRI data; and normalizing at least some of the second MRI data to produce normalized second MRI data, wherein combining the first MRI data and the second MRI data is performed using the normalized first MRI data and the normalized second MRI data.

8. The computerized system of claim 7, wherein normalizing the first MRI data and normalizing the second MRI data comprises using one or more of internal normalization, regional internal normalization and swapped regional internal normalization.

9. The computerized system of claim 7, wherein the method further comprises:

thresholding the normalized first MRI data to produce thresholded normalized first MRI data; and thresholding the normalized second MRI data to produce thresholded normalized second MRI data, wherein combining the normalized first MRI data and the second normalized MRI data is performed using the thresholded normalized first MRI data and the thresholded normalized second MRI data.

10. The computerized system of claim 9, wherein thresholding the normalized first MRI data comprises including in the thresholded normalized first MRI data only values that fall within two standard deviations from a mean value of the normalized first MRI data.

11. The computerized system of claim 9, wherein the method further comprises:

selecting a threshold value based, at least in part, on a type of MRI scan used to collect the first volumetric dataset and/or a neurological disease of the individual, and wherein thresholding the normalized first MRI data comprises applying the selected threshold value to the normalized first MRI data to produce the thresholded normalized first MRI data.

12. The computerized system of claim 1, wherein combining on a voxel-by-voxel basis, the first MRI data and the second MRI data to produce a volumetric injury map comprises:

generating, for each voxel, a weighted combination of the first MRI data and the second MRI data.

13. The computerized system of claim 12, wherein the method further comprises:

selecting a first weighting factor based on a type of MRI scan used to collect the first volumetric dataset; and selecting a second weighting factor based on a type of MRI scan used to collect the second volumetric dataset, wherein generating a weighted combination of the first MRI data and the second MRI data comprises combining the first MRI data weighted by the first weighting factor and the second MRI data weighted by the second weighting factor.

14. The computerized system of claim 13, wherein the first weighting factor and/or the second weighting factor are further selected based on a neurological disease of the individual.

15. The computerized system of claim 12, wherein generating a weighted combination of the first MRI data and the second MRI data for each voxel is based, at least in part, on a value of one or more other voxels in the first MRI data and/or the second MRI data.

16. The computerized system of claim 15, wherein the one or more other voxels include at least one voxel that neighbors the voxel for which the weighted combination is being generated.

17. The computerized system of claim 12, wherein generating a weighted combination of the first MRI data and the second MRI data for each voxel is based, at least in part, on a tissue type associated with the voxel.

18. The computerized system of claim 17, wherein the method further comprises:

applying a first weighting factor when the tissue type associated with the voxel is white matter; and applying a second weighting factor when the tissue type associated with the voxel is grey matter.

19. The computerized system of claim 1, wherein performing a structural-functional analysis of one or more brain networks or regions by refining the volumetric injury map using a volumetric eloquence map comprises:

combining, on a voxel-by-voxel basis, the volumetric injury map and the volumetric eloquence map to produce an injury mask.

20. The computerized system of claim 19, wherein combining, on a voxel-by-voxel basis, the first MRI data and the second MRI data to produce a volumetric injury map and combining, on a voxel-by-voxel basis, the volumetric injury map and the volumetric eloquence map are merged into a single step.

21. The computerized system of claim 19, wherein performing a structural-functional analysis of one or more brain networks or regions further comprises:
comparing the injury mask to a library of masks; and
determining the impact of the injury based on the comparison of the injury mask to the library of masks.

22. The computerized system of claim 21, wherein
each mask in the library of masks indicates grey matter nodes and white matter tracts for a structural-functional unit in the brain, and
determining the impact of the injury based on the comparison of the injury mask to the library of masks is further based on a spatial overlap between voxels in the injury mask and a structural-functional unit for a particular mask in the library of masks.

23. The computerized system of claim 1, wherein performing a structural-functional analysis of one or more brain networks or regions to determine an impact of injury within the one or more brain networks or regions comprises determining a location of voxels within the one or more brain networks or regions impacted by the injury.

24. The computerized system of claim 1, wherein performing a structural-functional analysis of one or more brain networks or regions to determine an impact of injury within the one or more brain networks or regions comprises determining a volume of the one or more brain networks or regions impacted by the injury.

25. The computerized system of claim 1, wherein the method further comprises:
estimating recoverability from the injury based, at least in part, on the structural-functional analysis and/or a tissue type.

26. The computerized system of claim 25, wherein
performing a structural-functional analysis of one or more brain networks or regions by refining the volumetric injury map using a volumetric eloquence map comprises combining, on a voxel-by-voxel basis, the volumetric injury map and the volumetric eloquence map to produce an injury mask, and
estimating recoverability from the injury comprises:
determining a proportion of voxels in the injury mask associated with white matter; and
estimating the recoverability from the injury based on the determined proportion of voxels in the injury mask associated with white matter.

27. A computer-implemented method for evaluating an impact of injury to brain networks or regions, the method comprising:
receiving magnetic resonance imaging (MRI) data of a brain of an individual, wherein the MRI data includes a first volumetric dataset recorded using first imaging parameters and a second volumetric dataset recorded using second imaging parameters;
combining, on a voxel-by-voxel basis, first MRI data based on the first volumetric dataset and second MRI data based on the second volumetric dataset to produce a volumetric injury map;
performing a structural-functional analysis of one or more brain networks or regions by refining the volumetric injury map using a volumetric eloquence map that specifies eloquent brain tissue within the one or more brain networks or regions to determine an impact of injury within the one or more brain networks or regions; and
displaying a visualization of the determined impact of injury within the one or more brain networks or regions.

28. A non-transitory computer-readable medium encoded with a plurality of instructions that, when executed, by at least one computer processor performs a method of evaluating an impact of injury to brain networks or regions, the method comprising:
receiving magnetic resonance imaging (MRI) data of a brain of an individual, wherein the MRI data includes a first volumetric dataset recorded using first imaging parameters and a second volumetric dataset recorded using second imaging parameters;
combining, on a voxel-by-voxel basis, first MRI data based on the first volumetric dataset and second MRI data based on the second volumetric dataset to produce a volumetric injury map;
performing a structural-functional analysis of one or more brain networks or regions by refining the volumetric injury map using a volumetric eloquence map that specifies eloquent brain tissue within the one or more brain networks or regions; and
displaying a visualization of the determined impact of injury within the one or more brain networks or regions.

* * * * *